US009169191B2

(12) United States Patent
Ma et al.

(10) Patent No.: US 9,169,191 B2
(45) Date of Patent: Oct. 27, 2015

(54) METHOD FOR SELECTIVE PREPARATION OF FATTY ACID MONO- AND DI-ESTERS OF ERYTHRITOL

(71) Applicant: Wilmar (Shanghai) Biotechnology Research & Development Center Co., LTD, Shanghai (CN)

(72) Inventors: Zonghui Ma, Shanghai (CN); Yan Zheng, Shanghai (CN); Tiankui Yang, Shanghai (CN); Xuebing Xu, Shanghai (CN)

(73) Assignee: Wilmar (Shanghai) Biotechnology Research & Development Center Co., LTD (CN)

( * ) Notice: Subject to any disclaimer, the term of this patent is extended or adjusted under 35 U.S.C. 154(b) by 0 days.

(21) Appl. No.: 14/403,509

(22) PCT Filed: May 24, 2013

(86) PCT No.: PCT/CN2013/076182
§ 371 (c)(1),
(2) Date: Nov. 24, 2014

(87) PCT Pub. No.: WO2013/174298
PCT Pub. Date: Nov. 28, 2013

(65) Prior Publication Data
US 2015/0119594 A1 Apr. 30, 2015

(30) Foreign Application Priority Data
May 25, 2012 (CN) .......................... 2012 1 0168150

(51) Int. Cl.
C07C 67/08 (2006.01)
C07C 69/33 (2006.01)
(Continued)

(52) U.S. Cl.
CPC . *C07C 67/08* (2013.01); *A61K 8/11* (2013.01); *A61K 8/375* (2013.01); *A61Q 19/00* (2013.01);
(Continued)

(58) Field of Classification Search
None
See application file for complete search history.

(56) References Cited

U.S. PATENT DOCUMENTS

| 3,951,945 A * | 4/1976 | Heesen ..................... A21D 2/14 |
| | | 536/18.2 |
| 2008/0051303 A1 * | 2/2008 | Brand ..................... C08K 5/103 |
| | | 508/100 |
| 2009/0162478 A1 | 6/2009 | Abend et al. |

FOREIGN PATENT DOCUMENTS

| CN | 1649664 A | 8/2005 |
| CN | 102524909 A | 7/2012 |

OTHER PUBLICATIONS

International Search Report Application No. PCT/CN2013/076182 Completed: Aug. 7, 2013; Mailing Date: Aug. 29, 2013 pp. 3.
Starks, "Phase-Transfer Catalysis. I. Heterogeneous Reactions Involving Anion Transfer by Quaternary Ammonium and Phosphonium Salts", Journal of the American Chemical Society / 93:I / Jan. 13, 1971, pp. 195-199.
(Continued)

*Primary Examiner* — Yate K Cutliff
(74) *Attorney, Agent, or Firm* — St. Onge Steward Johnston & Reens LLC

(57) ABSTRACT

The invention provides a method of preparing β-erythritol fatty acid monoester, including: subjecting a fatty acid and erythritol to esterification reaction in the presence of an acid catalyst, a water carrier and an optional phase transfer catalyst, wherein the molar ratio of the fatty acid to erythritol is 1:2 to 1:3, and the temperature of the esterification reaction is 80-100° C. In addition, the invention further provides a method of preparing 2,3-erythritol fatty acid diester, including: subjecting a fatty acid and erythritol to esterification reaction in the presence of an acid catalyst and a water carrier, wherein the molar ratio of the fatty acid to erythritol is 2:1 to 3:1, and the temperature of the esterification reaction is 120-160° C.

20 Claims, 1 Drawing Sheet

(51) Int. Cl.
- *A61K 8/37* (2006.01)
- *A61Q 19/00* (2006.01)
- *A61K 8/11* (2006.01)
- *A23L 1/00* (2006.01)
- *A23L 1/035* (2006.01)
- *A23L 1/22* (2006.01)

(52) U.S. Cl.
CPC ............... *C07C 69/33* (2013.01); *A23L 1/0029* (2013.01); *A23L 1/035* (2013.01); *A23L 1/22016* (2013.01); *A61K 2800/412* (2013.01)

(56) References Cited

OTHER PUBLICATIONS

Dehmlow, "Phase-Transfer Catalyzed Two-Phase Reactions in Preparative Organic Chemistry", Angew. Chem. infernat. Edit. / vol. 13 (1974), pp. 170-179.

Dockx, Jozef, "Quaternary Ammonium Compounds in Organic Synthesis", Synthesis, 1973, pp. 441-456.

Piao, et al., "Synthesis of mono- and dioleoyl erythritols through immobilized-lipase-catalyzed condensation of erythritol and oleic acid in acetone", Biochemical Engineering Journal 14 (2003) 79-84.

\* cited by examiner

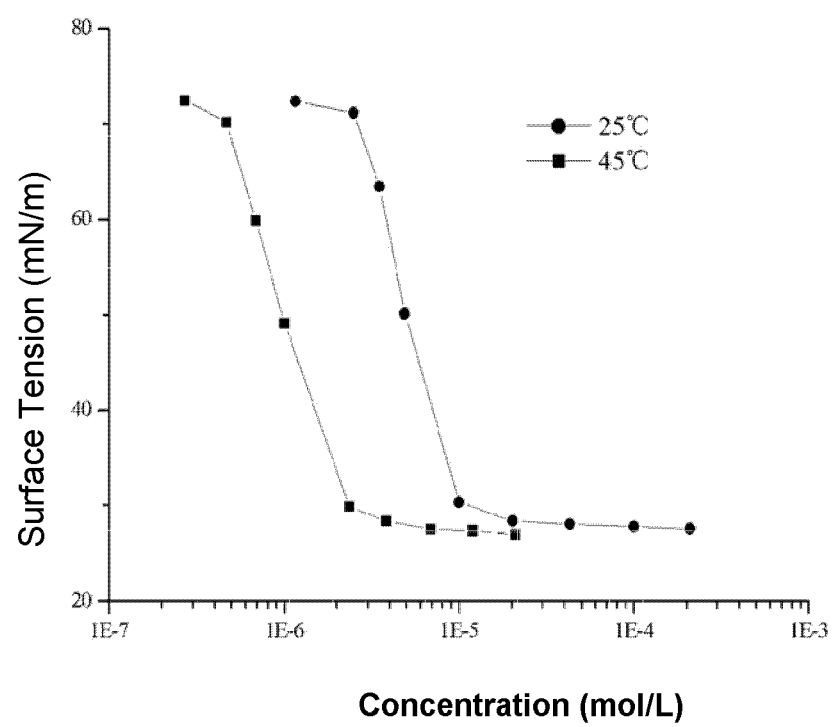

METHOD FOR SELECTIVE PREPARATION OF FATTY ACID MONO- AND DI-ESTERS OF ERYTHRITOL

TECHNICAL FIELD

The invention relates to esterification reaction. More particularly, the invention relates to a method for selective preparation of fatty acid mono- and di-esters of erythritol.

BACKGROUND ART

In recent years, as people's living standard rises, they have a growing demand on food's color, scent and taste. Good smell is one of the characteristics of food. However, the scent of some foods can not last long. Hence, fragrance or flavor needs to be incorporated in the course of food processing to augment the food's aroma. Nonetheless, fragrance and flavor obtained by extraction and refining often have such disadvantages as easy evaporation, poor storability, etc. In allusion to this problem, if fragrance and flavor are microcapsulated, the following advantages may be achieved: healthfulness, economy, performance stability, uniform scent, good storability, convenient use, etc. In the United States, powder flavor made by microcapsulation technology accounts for more than 50% of the food fragrance. Powder flavor is now widely used in cakes, solid beverage, solid soup, fast food and leisure food, such as baked products, confection products, soup powder, and the like. Particularly for baking occurring in high temperature environment which tends to damage or evaporate flavor, microcapsulation can reduce loss of flavor to a great extent.

However, the performance of these microcapsulated fragrance products can't fully meet people's requirements yet. For example, Ding Lizhong, et al elaborated the release mechanism of a microcapsule in "Development of Research on Microcapsulation of Food Flavor" published on China Condiment, No. 2, pp. 90-95, 2009. In the processing of baked food, flavor experiences a high temperature above 80° C. A conventional liposoluble wall material, a glycerin ester, melts prematurely during baking due to its low melting point (generally below 60° C.), leading to release of the embedded flavor. As such, loss of flavor is still noticeable notwithstanding its release is somewhat retarded by the wall of the microcapsule. Research and development are continued in an attempt to find wall materials for microcapsules to obtain more ideal slow release performance.

High purity fatty acid mono- and di-esters of erythritol are good wall materials for microcapsules, because they have relatively high melting points (about 80° C.) and thus can achieve better protection and slow-release of flavor embedded therein. Preparation of these two compounds via biocatalysis is known in the art. For example, Junkui Piao, et al disclosed in particular the synthesis of erythritol α-monooleate and erythritol 1,4-dioleate by enzymatic catalysis in a paper titled "Synthesis of Mono- and Di-oleoyl Erythritols through Immobilized-lipase-catalyzed Condensation of Erythritol and Oleic Acid in Acetone" and published on Biochemical Engineering Journal, Vol. 14, No. 2, pp. 79-84, May 2003. Up to date, preparation of high purity mono- and di-ester products of erythritol by a chemical esterification process rather than enzymatic catalysis has not been disclosed by any references in the art. For example, Chinese Patent Application CN1649664A mentioned use of fatty acid esters or polyesters of erythritol in applications such as cosmetics, etc, wherein tin chloride was used as a catalyst, and diester, triester and tetraester in the resulting products had similar proportions. This mixture of mono- to tetra-esters has a significantly lowered melting point, and has no remarkable comparative advantages over conventional glycerin esters. Therefore, a need exists for development of a new process for preparation of high purity mono- and di-esters of erythritol, which can realize high product selectivity as well as simplified process and reduced cost.

SUMMARY

In response to the technical need in the art as described above, in one aspect of the invention, there is provided a method of preparing β-erythritol fatty acid monoester, comprising: subjecting a fatty acid and erythritol to esterification reaction in the presence of an acid catalyst, a water carrier and an optional phase transfer catalyst, wherein the molar ratio of the fatty acid to erythritol is 1:2 to 1:3, and the temperature of the esterification reaction is 80-100° C. "Optional" means absence or presence.

In a preferred embodiment of the invention, the fatty acid used is a $C_8$-$C_{22}$ linear or branched, saturated or unsaturated fatty acid; more preferably, the fatty acid used is selected from octanoic acid, decanoic acid, myristic acid, lauric acid, palmitic acid, stearic acid, oleic acid, behenic acid, and combinations thereof.

In another preferred embodiment of the invention, the acid catalyst used is selected from inorganic acids, organosulfonic acids, solid acids, solid superacids, ion-exchange resins, and combinations thereof; more preferably, the inorganic acids are selected from sulfuric acid, boric acid, phosphoric acid, acidic salts of hydrochloric acid, bisulfates; the organosulfonic acids are selected from p-toluenesulfonic acid, sulfanilic acid; the solid acids are selected from MCM-41; the solid superacids are selected from s-/$Fe_3O_4$—$Al_2O_3$ type solid superacids; and the ion-exchange resins are selected from NKC-9 and Amberlyst 15.

In another preferred embodiment of the invention, the phase transfer catalyst used is selected from polyethers, quaternary ammonium salts or combinations thereof; more preferably, the polyethers are selected from polyethylene glycol and polyethylene glycol dialkyl ethers; and the quaternary ammonium salts are selected from tetrabutyl ammonium bromide, tetrabutyl ammonium chloride, dodecyl trimethyl ammonium chloride, tetradecyl trimethyl ammonium chloride and hexadecyl trimethyl ammonium bromide.

In another preferred embodiment of the invention, the water carrier used is selected from cyclohexane, toluene, xylene; more preferably, the water carrier is cyclohexane.

In another preferred embodiment of the invention, the esterification reaction lasts for 6-10 hours, preferably 7-9 hours.

In another preferred embodiment of the invention, the amount of the acid catalyst used is 1-20 wt %, preferably 1-5 wt %, based on the total weight of the fatty acid and erythritol used for the esterification reaction.

In another preferred embodiment of the invention, the amount of the phase transfer catalyst used is 1-10 wt %, based on the total weight of the fatty acid and erythritol used for the esterification reaction.

In another preferred embodiment of the invention, the selectivity of the esterification reaction to β-erythritol fatty acid monoester is equal to or higher than 90%.

In another preferred embodiment of the invention, the temperature of the esterification reaction is 90-100° C.

In a second aspect of the invention, there is provided a method of preparing 2,3-erythritol fatty acid diester, comprising: subjecting a fatty acid and erythritol to esterification reaction in the presence of an acid catalyst and a water carrier, wherein the molar ratio of the fatty acid to erythritol is 2:1 to 3:1, and the temperature of the esterification reaction is 120-160° C.

In another preferred embodiment of the invention, the fatty acid used is a $C_8$-$C_{22}$ linear or branched, saturated or unsaturated fatty acid; more preferably, the fatty acid is selected from octanoic acid, decanoic acid, myristic acid, lauric acid, palmitic acid, stearic acid, oleic acid, behenic acid, and combinations thereof.

In another preferred embodiment of the invention, the acid catalyst used is selected from inorganic acids, organosulfonic acids, solid acids, solid superacids, ion-exchange resins, and combinations thereof; more preferably, the inorganic acids are selected from sulfuric acid, boric acid, phosphoric acid, acidic salts of hydrochloric acid, bisulfates; the organosulfonic acids are selected from p-toluenesulfonic acid, sulfanilic acid; the solid acids are selected from MCM-41; the solid superacids are selected from s-/$Fe_3O_4$—$Al_2O_3$ type solid superacids; and the ion-exchange resins are selected from NKC-9 and Amberlyst 15.

In another preferred embodiment of the invention, the water carrier used is selected from cyclohexane, toluene, xylene. More preferably, the water carrier is toluene or xylene.

In another preferred embodiment of the invention, the esterification reaction lasts for 20-26 hours, preferably 22-25 hours.

In another preferred embodiment of the invention, the amount of the acid catalyst used is 1-10 wt %, based on the total weight of the fatty acid and erythritol used for the esterification reaction.

In another preferred embodiment of the invention, the selectivity of the esterification reaction to 2,3-erythritol fatty acid diester is equal to or higher than 90%.

In another preferred embodiment of the invention, the temperature of the esterification reaction is 120-140° C.

DESCRIPTION OF DRAWING

FIG. 1 shows surface tension vs. concentration curves of erythritol β-monooleate prepared according to the method of the invention.

DETAILED DESCRIPTION OF THE INVENTION

Unless otherwise specified, all percentages and proportions in this disclosure are based on mass. In addition, all numerical ranges described herein include endpoint values, and the upper and lower limits of the ranges disclosed may be combined with each other optionally to form new numerical ranges. For example, if the mass percentage of a component is disclosed to be 10-30 mass %, preferably 15-25 mass %, more preferably 20-23 mass %, then the following numerical ranges are disclosed equivalently at the same time: 10-15 mass %, 10-25 mass %, 10-20 mass %, 10-23 mass %, 15-30 mass %, 15-20 mass %, 15-23 mass %, 20-25 mass %, 23-25 mass %.

According to the invention, β-erythritol fatty acid monoester and 2,3-erythritol fatty acid diester may be prepared with high selectivity by carefully controlling the raw material proportions, the concentrations of the components in the reaction system, the type and amount of the catalyst, the reaction temperature and the reaction time. As used herein, "selectivity" refers to the molar percentage of a particular fatty acid ester produced based on the total moles of the erythritol that undergoes esterification reaction. In an embodiment of the method of preparing β-erythritol fatty acid monoester according to the invention, the selectivity of the product β-erythritol fatty acid monoester is equal to or higher than 90%. In an embodiment of the method of preparing 2,3-erythritol fatty acid diester according to the invention, the selectivity of the product 2,3-erythritol fatty acid diester is equal to or higher than 90%.

In an embodiment of the invention, β-erythritol fatty acid monoester or 2,3-erythritol fatty acid diester is prepared using $C_8$-$C_{22}$ linear or branched, saturated or unsaturated fatty acids. In the invention, the term "fatty acid" includes fatty acid and fatty oil as generally defined. For example, a long-chain fatty acid discovered in natural fats and oils comprises a compound having a linear or branched aliphatic chain and one or more acid groups such as carboxylate group, sulfonate group, phosphate group, phosphonate group, etc. The "fatty acid" compound can be "esterified" or react with hydroxyl group on a polyol to form a similar chemical bond. The fatty acid may be derived from a suitable natural or synthetic fatty acid or oil, which may be saturated or unsaturated, or may be a linear or branched fatty acid, and may optionally comprise a positional or geometric isomer. A variety of fatty acids or oils are commercially available, or may be prepared or separated easily using the procedures known to those skilled in the art. The fatty acid is preferably a linear fatty acid. Examples of a suitable fatty acid include those selected from octanoic acid, decanoic acid, myristic acid, lauric acid, palmitic acid, stearic acid, oleic acid, behenic acid, and mixtures thereof. Palmitic acid, octanoic acid, behenic acid, oleic acid, and mixtures thereof are more preferred. Correspondingly, the term "$C_8$-$C_{22}$ fatty acid" refers to a fatty acid comprising 8, 9, 10, 11, 12, 13, 14, 15, 16, 17, 18, 19, 20, 21 or 22 carbon atoms.

In an embodiment of the invention, as to the method of preparing β-erythritol fatty acid monoester, the molar ratio of the fatty acid to erythritol is 1:2 to 1:3; the esterification temperature is 80-100° C., preferably 90-100° C.; and the esterification time is 6-10 hours, preferably 7-9 hours, more preferably 8 hours. In an embodiment of the invention, as to the method of preparing 2,3-erythritol fatty acid diester, the molar ratio of the fatty acid to erythritol is 2:1 to 3:1; the esterification temperature is 120-160° C., preferably 120-140° C.; and the esterification time is 20-26 hours, preferably 22-25 hours, more preferably 24 hours.

In the invention, "an acid catalyst" refers to a substance capable of providing a proton as defined by Bronsted, or a substance capable of forming a covalent bond with an atom, molecule or ion having a pair of unshared electrons as defined by Lewis. The acid catalyst used in the invention may be selected from inorganic acids, organosulfonic acids, solid acids, solid superacids, ion-exchange resins, and combinations thereof. The inorganic acids may be selected from sulfuric acid, boric acid, phosphoric acid, acidic salts of hydrochloric acid, bisulfates; the organosulfonic acids may be selected from p-toluenesulfonic acid, sulfanilic acid; the solid acids may be selected from MCM-41; the solid superacids may be selected from s-/$Fe_3O_4$—$Al_2O_3$ type solid superacids; and the ion-exchange resins may be selected from NKC-9 and Amberlyst 15. The acid catalyst is preferably p-toluenesulfonic acid, s-/$Fe_3O_4$—$Al_2O_3$ type solid superacid, NKC-9, sulfuric acid, or a mixture thereof.

In the invention, the term "phase transfer catalyst" refers to a substance which is at least partially present in a first phase (generally organic phase), or wetted by the first phase, and capable of promoting reaction between a reactant in the first phase and another reactant transferred from a second phase (generally an aqueous phase, but in some cases it is solid) to the first phase. After the reaction, the phase transfer catalyst is released to transfer the reactant further. E. V. Dehmlow reviewed phase transfer catalysts in Angewante Chemie (int'l ver.), 13(3), 170(1974). See Jozef Dockx, Synthesis (1973), 441-456 and C. M. Starks, JACS., (93)1, 195-199, Jan. 13, 1971 for other related reviews. A suitable phase transfer catalyst is preferably a quaternary ammonium salt or a polyether comprising a bulky organic group to facilitate its dissolution in an organic phase, wherein the bulky organic group is generally an alkyl or arylalkyl group. A preferred phase transfer catalyst is a tetraalkyl or arylalkyl(e.g. benzyl)trialkyl ammonium or polyether, wherein the number of carbon atoms attached to each nitrogen atom or phosphorus atom is 10-70, most preferably 16-40. In the reaction system of the invention, a phase transfer catalyst may be used optionally to facilitate transfer of a reactant between a hydrophobic phase and a hydrophilic phase to promote the reaction. In an embodiment of the invention, as to the method of preparing β-erythritol fatty acid monoester, the phase transfer catalyst used therein is selected from polyethers and quaternary ammonium salts. The polyethers are selected from polyethylene glycol and polyethylene glycol dialkyl ethers; and the quaternary ammonium salts are selected from tetrabutyl ammonium bromide, tetrabutyl ammonium chloride, dodecyl trimethyl ammonium chloride, tetradecyl trimethyl ammonium chloride and hexadecyl trimethyl ammonium bromide.

As the esterification reaction in the invention is reversible, addition of a water carrier may help the reaction proceed in a forward direction to generate an ester. The term "water carrier" refers to a substance capable of removing water generated by a reaction from a reaction system. It can form a binary or ternary azeotrope with water or one of the reactants such that the water may be carried out of the reaction system in time. Consequently, the thermodynamic equilibrium is broken, and the reaction advances toward formation of an ester. In an embodiment of the invention, according to the method of preparing the mono- and di-esters, the water carrier is selected from cyclohexane, toluene and xylene. In another embodiment of the invention, the water carrier is preferably cyclohexane for preparation of β-erythritol fatty acid monoester. In another embodiment of the invention, the water carrier is preferably toluene or xylene in the method of preparing 2,3-erythritol fatty acid diester.

In an embodiment of the invention, as to the method of preparing β-erythritol fatty acid monoester, the amount of the acid catalyst used is 1-20 wt %, preferably 7-12 wt %, more preferably 1-5 wt %, based on the total weight of the fatty acid and erythritol used for the esterification reaction. As to the method of preparing 2,3-erythritol fatty acid diester, the amount of the acid catalyst used is 1-10 wt %, based on the total weight of the fatty acid and erythritol used for the esterification reaction.

After reading the above specification, those skilled in the art can modify, substitute and combine the above embodiments to a certain extent within the scope covered by the art, so as to implement the invention and produce similar technical effects. All these modifications, substitutions and combinations are included within the scope of the invention, too.

Preferred embodiments of the invention will be illustrated in more detail with reference to the following specific examples in order for the invention to be understood more deeply and precisely. Nevertheless, it is to be noted that the following specific examples are only intended for illustration, not for limiting in any way the protection scope of the invention which is defined only by the claims.

EXAMPLES

First, selective preparation of β-erythritol fatty acid monoester will be illustrated with reference to the following Examples 1-6.

Example 1

Preparation of Erythritol β-Monopalmitate 105 g (0.41 mol) palmitic acid and 150 g (1.23 mol) erythritol were added into a 2 L three-neck flask which was equipped with a stirrer, a condenser and an addition funnel. To this flask was added 1 L cyclohexane as a water carrier, followed by addition of a phase transfer catalyst hexadecyl trimethyl ammonium bromide (7.65 g, 3 wt %) and a reaction catalyst p-toluenesulfonic acid (5.1 g, 2 wt %). An oil bath device was used to heat the mixture to 94±2° C. and reflux it at this temperature for 6 hours. Since the melting point of erythritol is 122° C., when the reaction was ended, unreacted erythritol in solid form could be observed in the reaction system. The unreacted erythritol was filtered off when it was still hot. Subsequently, the reaction system was allowed to cool to room temperature and stand for 2 hours. A portion of the product was obtained in solid form by filtration. The filtrate was dried by rotary evaporation, and the resultant product was combined with the solid obtained previously by filtration. An 80 g solid product was obtained in total after washing with a saturated sodium bicarbonate aqueous solution and petroleum ether in sequence. $^1$H NMR characterization of a solution of the product in $CDCl_3$ was conducted using a Bruker-400 nuclear magnetic resonance spectromer available from Bruker, Swiss, and the results are as follows: δ 0.88 (3H, t, J=6.8 Hz), 1.25 (24H, m), 1.64 (2H, m), 2.39 (2H, t, J=7.6 Hz), 3.71 (1H, dd, J=5.6 Hz), 3.81 (1H, dd, J=4 Hz), 3.97 (1H, dd, J=5.6 Hz), 4.07 (1H, dd, J=5.6 Hz), 4.45 (1H, m), 5.14 (1H, m). The above NMR data show that the product obtained was a monoester generated by esterification of the hydroxyl group on the 0 position of erythritol, i.e. erythritol β-monopalmitate. As characterized using Agilent 1200 HPLC (using an ELSD detector) available from Agilent Co., USA, the purity of erythritol β-monopalmitate in the product was 91%.

In the following examples, similar reaction devices were used, and the same instruments and procedures were used for qualitative and quantitative analysis of the products.

Example 2

Preparation of Erythritol β-Monopalmitate 10.5 g (0.041 mol) palmitic acid and 15 g (0.123 mol) erythritol were added into a 500 mL three-neck flask which was equipped with a stirrer, a condenser and an addition funnel. To this flask was added 200 mL cyclohexane as a water carrier, followed by addition of a reaction catalyst NKC-9 (NKC-9 dry hydrogen catalytic resin, available from Nanda Resin Plant) (5 g, 20 wt %). The mixture was refluxed at 85±2° C. for 10 hours. When the reaction was ended, the reaction system was allowed to cool to room temperature and stand for 2 hours. The catalyst and the excessive erythritol were filtered off, and 5 g product was obtained after drying by rotary evaporation. The product was erythritol β-monopalmitate as characterized by $^1$H NMR, and the purity was 93% as characterized by HPLC.

Example 3

Preparation of Erythritol β-Monopalmitate 10.5 g (0.041 mol) palmitic acid and 15 g (0.123 mol) erythritol were added into a 500 mL three-neck flask which was equipped with a stirrer, a condenser and an addition funnel. To this flask was added 200 mL cyclohexane as a water carrier, followed by addition of a phase transfer catalyst polyethylene glycol dialkyl ether (2.6 g, 10 wt %) and a reaction catalyst s-/$Fe_3O_4$—$Al_2O_3$ type solid superacid (available from Xiamen Xindakang Inorganic Material Co., Ltd) (1.28 g, 5 wt %). The mixture was refluxed at 88±2° C. for 8 hours. When the reaction was ended, the reaction system was allowed to cool to room temperature and stand for 2 hours. The catalyst and the excessive erythritol were filtered off, and 8 g product was obtained after drying by rotary evaporation. The product was erythritol β-monopalmitate as characterized by $^1H$ NMR, and the purity was 91% as characterized by HPLC.

Example 4

Preparation of Erythritol β-Monooctanoate 14.4 g (0.1 mol) octanoic acid and 24.4 g (0.2 mol) erythritol were added into a 500 mL three-neck flask which was equipped with a stirrer, a condenser and an addition funnel. To this flask was added 200 mL cyclohexane as a water carrier, followed by addition of a phase transfer catalyst polyethylene glycol (available from Sinopharm Chemical Reagent Co., Ltd) (1.17 g, 3 wt %) and a reaction catalyst phosphoric acid (0.4 g, 1 wt %). The mixture was refluxed at 96±2° C. for 9 hours. When the reaction was ended, the reaction system was allowed to cool to room temperature and stand for 2 hours. The catalyst and the excessive erythritol were filtered off, and 10 g product was obtained after drying by rotary evaporation. The product was erythritol β-monooctanoate as characterized by $^1H$ NMR, and the purity was 92% as characterized by HPLC.

Example 5

Preparation of Erythritol β-Monooleate 50 g (0.18 mol) oleic acid and 65 g (0.54 mol) erythritol were added into a 1 L three-neck flask which was equipped with a stirrer, a condenser and an addition funnel. To this flask was added 500 mL cyclohexane as a reflux solvent, followed by addition of a phase transfer catalyst tetramethyl ammonium bromide (4.6 g, 4 wt %) and a reaction catalyst p-toluenesulfonic acid (3.45 g, 3 wt %). The mixture was refluxed at 98±2° C. for 8 hours. The unreacted erythritol was filtered off when it was still hot. After cooling and standing for 2 hours, the precipitated solid product was collected by filtration. The liquid phase was washed with a saturated sodium bicarbonate aqueous solution and petroleum ether in sequence, and a solid product was obtained after rotary evaporation. This solid product was combined with the solid product obtained previously by filtration, affording a 30 g solid product in total. A solution of the product in $CDCl_3$ was characterized by $^1H$ NMR (400 MHz), and the results are as follows: δ 0.88 (3H, t, J=6.8 Hz), 1.29 (20H, m), 1.64 (2H, m), 2.1 (4H, m), 2.37 (2H, m), 3.66 (1H, m), 3.81 (2H, m), 3.89 (1H, m), 5.13 (2H, m), 5.35 (2H, t, J=5.6 Hz). The above NMR data show that the product obtained was a monoester generated by esterification of the hydroxyl group on the 0 position of erythritol, i.e. erythritol β-monooleate. The purity was determined by HPLC to be 92%.

Example 6

Preparation of Erythritol β-Monobehenate 34 g (0.1 mol) behenic acid and 36.6 g (0.3 mol) erythritol were added into a 1 L three-neck flask which was equipped with a stirrer, a condenser and an addition funnel. To this flask was added 500 mL cyclohexane as a water carrier, followed by addition of a phase transfer catalyst dodecyl trimethyl ammonium chloride (2.1 g, 3 wt %) and a reaction catalyst sulfanilic acid (1.4 g, 2 wt %). The mixture was refluxed at 94±2° C. for 8 hours. After cooling and standing, the catalyst and the excessive erythritol were filtered off, and 20 g product was obtained after drying by rotary evaporation. The product was erythritol β-monobehenate as characterized by $^1H$ NMR, and the purity was 93% as characterized by HPLC.

Example 7

Critical Micelle Concentration (CMC) of Erythritol β-Monooleate Measured by Surface Tension Method In order to demonstrate the difference in properties between β-erythritol fatty acid monoester prepared according to the invention and α-erythritol fatty acid monoester prepared according to the prior art, the critical micelle concentration of an aqueous solution of the product prepared in Example 5 was measured by a surface tension method. The specific procedure was as follows:

The erythritol β-monooleate prepared in Example 5 was dissolved in water to formulate a $10^{-3}$ mol/L mother solution which was then diluted stepwise with water to obtain a series of aqueous solutions in the range of $10^{-3}$~$10^{-7}$ mol/L.

The surface tension values were determined by the ring method at a constant temperature (25° C. and 45° C. respectively in the invention) using a K100 surface tensiometer available from Kruss Co. Each sample was measured three times, and an average was taken.

FIG. 1 shows the curves of the surface tension measured as a function of the concentration, wherein the x-axis represents the concentration (mol/L), and the y-axis represents the surface tension value (mN/m). In the FIGURE, the point at which the slope of the curve changes abruptly corresponds to a surfactant concentration which is the CMC value.

As indicated by FIG. 1, the CMC value of erythritol β-monooleate is $2.73 \times 10^{-5}$ at 25° C. and $2.47 \times 10^{-6}$ at 45° C. A comparison with the CMC values of erythritol α-monooleate prepared in the literature of Junkui Piao, et al shows that the CMC of β-monoester is smaller than that of α-monoester. That's to say, β-erythritol fatty acid monoester exhibits a better surface activity.

Examples 8-10 below demonstrate specific embodiments of preparing 2,3-erythritol fatty acid diester according to the method of the invention.

Example 8

Preparation of Erythritol 2,3-Dipalmitate 210 g (0.82 mol) palmitic acid and 50 g (0.41 mol) erythritol were added into a 2 L three-neck flask which was equipped with a stirrer, a condenser and an addition funnel. To the flask was added 1 L toluene as a water carrier, followed by addition of a reaction catalyst p-toluenesulfonic acid (7.8 g, 3 wt %). An oil bath device was used to heat the mixture to 125±2° C. and reflux it at this temperature for 24 hours. When the reaction was ended, the reaction system was allowed to cool to room temperature and stand for 2 hours. The solid was removed by filtration, and the liquid phase was washed with a saturated sodium bicarbonate aqueous solution and petroleum ether in sequence. A 220 g solid product was obtained after drying by rotary evaporation. A solution of the product in CDCl$_3$ was characterized by $^1$H NMR (400 MHz), and the results are as follows: δ 0.88 (3H, t, J=6.8 Hz), 1.26 (48H, m), 1.61 (4H, m), 2.32 (4H, t, J=7.6 Hz), 3.80 (2H, dd, J=4 Hz), 4.08 (2H, dd, J=5.6 Hz), 5.32 (2H, m). The above results show that the product obtained was a product formed by esterification of the hydroxyl groups on the 2,3-positions of erythritol, i.e. erythritol dipalmitate. The purity was determined by HPLC to be 92%.

Example 9

Preparation of Erythritol 2,3-Dioleate 347 g (1.23 mol) oleic acid and 50 g (0.41 mol) erythritol were added into a 2 L three-neck flask which was equipped with a stirrer, a condenser and an addition funnel. To the flask was added 1 L toluene as a water carrier, followed by addition of a reaction catalyst p-toluenesulfonic acid (7.9 g, 2 wt %). The mixture was refluxed at 135±2° C. for 26 hours. When the reaction was ended, the reaction system was allowed to cool to room temperature and stand for 2 hours. The solid was removed by filtration, and the liquid phase was washed with a saturated sodium bicarbonate aqueous solution and petroleum ether in sequence. 160 g solid product was obtained after drying by rotary evaporation. A solution of the product in (CD$_3$)$_2$CO was tested by 1H NMR (400 MHz), and the results are as follows: (400 MHz): δ 0.89 (3H, t, J=6.8 Hz), 1.30 (20H, m), 1.60 (4H, m), 2.05 (8H, m), 2.34 (4H, t, J=7.6 Hz), 3.72 (2H, dd, J=4 Hz), 4.02 (2H, dd, J=5.6 Hz), 5.36 (6H, m). The above results show that the product obtained was a product formed by esterification of the hydroxyl groups on the 2,3-positions of erythritol, i.e. erythritol dioleate. The purity was determined by HPLC to be 91%.

Example 10

Preparation of Erythritol 2,3-Dibehenate 340 g (1 mol) behenic acid and 61 g (0.5 mol) erythritol were added into a 2 L three-neck flask which was equipped with a stirrer, a condenser and an addition funnel. To the flask was added 1 L xylene as a water carrier, followed by addition of a reaction catalyst sulfuric acid (32 g, 8 wt %). The mixture was refluxed at 145±2° C. for 22 hours. When the reaction was ended, the reaction system was allowed to cool to room temperature and stand for 2 hours. The solid was removed by filtration, and the liquid phase was washed with a saturated sodium bicarbonate aqueous solution and petroleum ether in sequence. 260 g solid product was obtained after drying by rotary evaporation. The product was erythritol 2,3-dibehenate as characterized by $^1$H NMR, and the purity was 91% as characterized by HPLC.

In summary, the method of the invention may be used to synthesize high purity fatty acid mono- and di-esters of erythritol by controlling the raw material proportions, the concentrations of the reaction system, the amount of the catalyst, the temperature and the reaction time; and the products obtained exhibit positional selectivity as shown by the NMR results.

We have discovered further that the products prepared according to the invention have better performances and wider commercial uses. For example, the chemical catalytic process in the prior art can only afford a mixture of monoester, diester, triester and tetraester. As compared with a mixture, high purity fatty acid monoester and diester of erythritol have higher melting points. Hence, when they are used in a wall material for microcapsules, better slow release performance can be obtained.

On the other hand, the products prepared according to the prior art biological enzymatic catalytic process are α-erythritol fatty acid monoester and 1,4-erythritol fatty acid diester. As indicated by the above CMC experimental results, β-erythritol fatty acid monoester exhibits a better surface activity than α-erythritol fatty acid monoester. In addition, when fatty acid diester of erythritol is used for food, 1,4-erythritol fatty acid diester is susceptible to hydrolyzation by pancreatic lipase because pancreatic lipase can only hydrolyze a primary alcohol ester in a specific way. In contrast, 2,3-erythritol fatty acid diester can't be hydrolyzed by pancreatic lipase, and thus is more suitable for diabetes patients. In other words, the two methods of the invention can afford, with high selectivity, β-erythritol fatty acid monoester and 2,3-erythritol fatty acid diester products having better properties, and have a significant effect in promoting commercial application and marketing.

What is claimed is:
1. A method of preparing β-erythritol fatty acid monoester, comprising: subjecting a fatty acid and erythritol to esterification reaction in the presence of an acid catalyst, a water carrier and an optional phase transfer catalyst, wherein the molar ratio of the fatty acid to erythritol is 1:2 to 1:3, and the temperature of the esterification reaction is 80-100° C.

2. The method of claim 1, wherein the fatty acid is a C$_8$-C$_{22}$ linear or branched, saturated or unsaturated fatty acid.

3. The method of claim 2, wherein the fatty acid is selected from a group consisting of octanoic acid, decanoic acid, myristic acid, lauric acid, palmitic acid, stearic acid, oleic acid, behenic acid, and combinations thereof.

4. The method of claim 1, wherein the acid catalyst is selected from a group consisting of inorganic acids, organosulfonic acids, solid acids, solid superacids, ion-exchange resins, and combinations thereof.

5. The method of claim 4, wherein the inorganic acids are selected from a group consisting of sulfuric acid, boric acid, phosphoric acid, acidic salts of hydrochloric acid, bisulfates; the organosulfonic acids are selected from a group consisting of p-toluenesulfonic acid, sulfanilic acid; the solid acids are selected from a group consisting of MCM-41; the solid superacids are selected from a group consisting of s-/Fe$_3$O$_4$—Al$_2$O$_3$ type solid superacids; and the ion-exchange resins are selected from a group consisting of NKC-9 and Amberlyst 15.

6. The method of claim 1, wherein the phase transfer catalyst is selected from a group consisting of polyethers, quaternary ammonium salts, and combinations thereof.

7. The method of claim 1, wherein the water carrier is selected from a group consisting of cyclohexane, toluene and xylene.

8. The method of claim 1, wherein the amount of the acid catalyst used is 1-20 wt %, based on the total weight of the fatty acid and erythritol used for the esterification reaction.

9. The method of claim 1, wherein the amount of the phase transfer catalyst used is 1-10 wt %, based on the total weight of the fatty acid and erythritol used for the esterification reaction.

10. The method of claim 1, wherein the selectivity of the esterification reaction to β-erythritol fatty acid monoester is equal to or higher than 90%.

11. The method of claim 1, wherein the temperature of the esterification reaction is 90-100° C.

12. A method of preparing 2,3-erythritol fatty acid diester, comprising: subjecting a fatty acid and erythritol to esterification reaction in the presence of an acid catalyst and a water carrier, wherein the molar ratio of the fatty acid to erythritol is 2:1 to 3:1, and the temperature of the esterification reaction is 120-160° C.

13. The method of claim 12, wherein the fatty acid is a $C_8$-$C_{22}$ linear or branched, saturated or unsaturated fatty acid.

14. The method of claim 13, wherein the fatty acid used is selected from a group consisting of octanoic acid, decanoic acid, myristic acid, lauric acid, palmitic acid, stearic acid, oleic acid, behenic acid, and combinations thereof.

15. The method of claim 12, wherein the acid catalyst is selected from a group consisting of inorganic acids, organosulfonic acids, solid acids, solid superacids, ion-exchange resins, and combinations thereof.

16. The method of claim 15, wherein the inorganic acids are selected from a group consisting of sulfuric acid, boric acid, phosphoric acid, acidic salts of hydrochloric acid, bisulfates; the organosulfonic acids are selected from a group consisting of p-toluenesulfonic acid, sulfanilic acid; the solid acids are selected from a group consisting of MCM-41; the solid superacids are selected from a group consisting of s-/$Fe_3O_4$—$Al_2O_3$ type solid superacids; and the ion-exchange resins are selected from NKC-9 and Amberlyst 15.

17. The method of claim 12, wherein the water carrier is selected from a group consisting of cyclohexane, toluene and xylene.

18. The method of claim 12, wherein the amount of the acid catalyst used is 1-10 wt %, based on the total weight of the fatty acid and erythritol used for the esterification reaction.

19. The method of claim 12, wherein the selectivity of the esterification reaction to 2,3-erythritol fatty acid diester is equal to or higher than 90%.

20. The method of claim 12, wherein the temperature of the esterification reaction is 120-140° C.

* * * * *